United States Patent [19]

Jahnsen

[11] Patent Number: 5,097,026

[45] Date of Patent: Mar. 17, 1992

[54] DNA FOR HUMAN REGULATORY SUBUNITS (RIα AND RIIβ) OF CAMP-DEPENDENT PROTEIN KINASES

[76] Inventor: Tore Jahnsen, Atriumveien 10L, Ski, Norway, N-1400

[21] Appl. No.: 216,715

[22] PCT Filed: Oct. 27, 1987

[86] PCT No.: PCT/NO87/00069

§ 371 Date: Jun. 28, 1988

§ 102(e) Date: Jun. 28, 1988

[87] PCT Pub. No.: WO88/03164

PCT Pub. Date: May 5, 1988

[30] Foreign Application Priority Data

Oct. 28, 1986 [NO] Norway .................. 864301

[51] Int. Cl.$^5$ .............................. C12N 15/12
[52] U.S. Cl. ................... 536/27; 435/320.1
[58] Field of Search ............ 536/27; 435/320, 320.1

[56] References Cited

PUBLICATIONS

Jahnsen, T. et al., "Molecular Cloning, cDNA Structure, and Regulation of Regulatory Subunit of Type II cAMP Kinase . . . ", J. Biol. Chem. 261(26), pp. 12352–12361, 6/15/86.

Weber, W. "Isolation of a 50,000 Dalton cAMP Binding Protein . . . ", Biochem. Biophys. Research Comm. 104(3) pp. 1134–1141, 2/11/82.

Kapoor, C. et al., "Mitotic Apparatus and Nucleoli Compartmentalization of a 50,000 Dalton Type II . . . ", Chem. Abstracts 98 141023v 4/25/83.

Young & Davis "Efficient Isolation of Genes by Using Antibody Probes", Proc. Natl. Acad. Sci. U.S.A. vol. 80, pp. 1194–1198, 3/83.

Cosgrove et al. "A genomic Clone Encoding the α Chain of the OKM1, LFA-1 . . . ", Proc. Natl. Acad. Sci. U.S.A. vol. 83, pp. 752–756, 2/86.

*Primary Examiner*—Margaret Moskowitz
*Assistant Examiner*—Nina Ossanna
*Attorney, Agent, or Firm*—Fleit, Jacobson, Cohn, Price, Holman & Stern

[57] ABSTRACT

Complementary DNA (cDNA) probes or fragments derived from these for human regulatory subunits of cAMP-dependent protein kinases. Human cDNA's for regulatory subunits (RIα and RIIβ) of cAMP-dependent protein kinases have been identified and cloned.

3 Claims, 6 Drawing Sheets

```
  1 GCAGAGTGGAGCGGGGCTGGGAGCAAAGCGCTGAGGGAGCTCGGTACGCCGCCGCCTCGC  60
 61 ACCCGCAGCCTCGCGCCCGCCGCCGCCCGTCCCCAGAGAACCATGGAGTCTGGCAGTACC 120
                                            MetGluSerGlySerThr
121 GCCGCCAGTGAGGAGGCACGCAGCCTTCGAGAATGTGAGCTCTACGTCCAGAAGCATAAC 180
    AlaAlaSerGluGluAlaArgSerLeuArgGluCysGluLeuTyrValGlnLysHisAsn
181 ATTCAAGCACTGCTCAAAGATTCTATTGTGCAGTTGTGCACTGCTCGACCTGAGAGACCC 240
    IleGlnAlaLeuLeuLysAspSerIleValGlnLeuCysThrAlaArgProGluArgPro
241 ATGGCATTCCTCAGGGAATACTTTGAGAGGTTGGAGAAGGAGGAGGCAAAACAGATTCAG 300
    MetAlaPheLeuArgGluTyrPheGluArgLeuGluLysGluGluAlaLysGlnIleGln
301 AATCTGCAGAAAGCAGGCACTCGTACAGACTCAAGGGAGGATGAGATTTCTCCTCCTCCA 360
    AsnLeuGlnLysAlaGlyThrArgThrAspSerArgGluAspGluIleSerProProPro
361 CCCAACCCAGTGGTTAAAGGTAGGAGGCGACGAGGTGCTATCAGCGCTGAGGTCTACACG 420
    ProAsnProValValLysGlyArgArgArgArgGlyAlaIleSerAlaGluValTyrThr
421 GAGGAAGATGCGGCATCCTATGTTAGAAAGGTTATACCAAAAGATTACAAGACAATGGCC 480
    GluGluAspAlaAlaSerTyrValArgLysValIleProLysAspTyrLysThrMetAla
481 GCTTTAGCCAAAGCCATTGAAAAGAATGTGCTGTTTTCACATCTTGATGATAATGAGAGA 540
    AlaLeuAlaLysAlaIleGluLysAsnValLeuPheSerHisLeuAspAspAsnGluArg
541 AGTGATATTTTTGATGCCATGTTTTCGGTCTCCTTTATCGCAGGAGAGACTGTGATTCAG 600
    SerAspIlePheAspAlaMetPheSerValSerPheIleAlaGlyGluThrValIleGln
601 CAAGGTGATGAAGGGGATAACTTCTATGTGATTGATCAAGGAGAGACGGATGTCTATGTT 660
    GlnGlyAspGluGlyAspAsnPheTyrValIleAspGlnGlyGluThrAspValTyrVal
661 AACAATGAATGGGCAACCAGTGTTGGGGAAGGAGGGAGCTTTGGAGAACTTGCTTTGATT 720
    AsnAsnGluTrpAlaThrSerValGlyGluGlyGlySerPheGlyGluLeuAlaLeuIle
```

FIG. 1A

```
721  TATGGAACACCGAGAGCAGCCACTGTCAAAGCAAAGACAAATGTGAAATTGTGGGGCATC 780
     TyrGlyThrProArgAlaAlaThrValLysAlaLysThrAsnValLysLeuTrpGlyIle

781  GACCGAGACAGCTATAGAAGAATCCTCATGGGAAGCACACTGAGAAAGCGGAAGATGTAT 840
     AspArgAspSerTyrArgArgIleLeuMetGlySerThrLeuArgLysArgLysMetTyr

841  GAGGAATTCCTTAGTAAAGTCTCTATTTTAGAGTCTCTGGACAAGTGGGAACGTCTTACG 900
     GluGluPheLeuSerLysValSerIleLeuGluSerLeuAspLysTrpGluArgLeuThr

901  GTAGCTGATGCATTGGAACCAGTGCAGTTTGAAGATGGGCAGAAGATTGTGGTGCAGGGA 960
     ValAlaAspAlaLeuGluProValGlnPheGluAspGlyGlnLysIleValValGlnGly

961  GAACCAGGGGATGAGTTCTTCATTATTTTAGAGGGGTCAGCTGCTGTGCTACAACGTCGG 1020
     GluProGlyAspGluPhePheIleIleLeuGluGlySerAlaAlaValLeuGlnArgArg

1021 TCAGAAAATGAAGAGTTTGTTGAAGTGGGAAGATTGGGGCCTTCTGATTATTTTGGTGAA 1080
     SerGluAsnGluGluPheValGluValGlyArgLeuGlyProSerAspTyrPheGlyGlu

1081 ATTGCACTACTGATGAATCGTCCTCGTGCTGCCACAGTTGTTGCTCGTGGCCCCTTGAAG 1140
     IleAlaLeuLeuMetAsnArgProArgAlaAlaThrValValAlaArgGlyProLeuLys

1141 TGCGTTAAGCTGGACCGACCTAGATTTGAACGTGTTCTTGGCCCATGCTCAGACATCCTC 1200
     CysValLysLeuAspArgProArgPheGluArgValLeuGlyProCysSerAspIleLeu

1201 AAACGAAACATCCAGCAGTACAACAGTTTTGTGTCACTGTCTGTCTGAAATCTGCCTCCT 1260
     LysArgAsnIleGlnGlnTyrAsnSerPheValSerLeuSerValEnd

1261 GTGCCTCCCTTTTCTCCTCTCCCCAATCCATGCTTCACTCATGCAAACTGCTTTATTTTC 1320

1321 CCTACTTGCAGCGCCAAGTGGCCACTGGCATCGCAGCTTCCTGTCTGTTTATATATTAAA 1380

1381 GTTGCTTTTATTGCACCATTTTCAATTTGGAGCATTAACTAAATGCTCATACACAGTTAA 1440

1441 ATAAATAGAAAGAGTTCTATGGAAAAAAAAAAAAA                         1475
```

FIG. 1B

```
  1 ACGCGCGCCGGGAGCCGGCGGCCGGGCCAGCCGGCGCCGGGGCCCAGTGCGCCGCGCTCG  60

61 CAGCCGGTAGCGCGCCAGCCGTAGGCGTCGCTCGGCAGCCGCGGGGCCCTAGGCGTGCCG 120

121 GGGAGGGGGCGAGGGCGGCCAGGCGCCTGCCGCCCCGGAGGCAGGATGAGCATCGAGATC 180
                                                  MetSerIleGluIle

181 CCGGCGGGACTGACGGAGCTGCTGCAGGGCTTCACGGTGGAGGTGCTGAGGCACCAGCCC 240
    ProAlaGlyLeuThrGluLeuLeuGlnGlyPheThrValGluValLeuArgHisGlnPro

241 GCGGACCTGCTGGAGTTCGCGCTGCAGCACTTCACCCGCCTGCAGCAGGAGAACGAGCGC 300
    AlaAspLeuLeuGluPheAlaLeuGlnHisPheThrArgLeuGlnGlnGluAsnGluArg

301 AAAGGCACCGCGCGCTTCGGCCATGAGGGCAGGACCTGGGGGGACCTGGGCGCCGCTGCC 360
    LysGlyThrAlaArgPheGlyHisGluGlyArgThrTrpGlyAspLeuGlyAlaAlaAla

361 GGGGGCGGCACCCCCAGCAAGGGGGTCAACTTCGCCGAGGAGCCCATGCAGTCCGACTCC 420
    GlyGlyGlyThrProSerLysGlyValAsnPheAlaGluGluProMetGlnSerAspSer

421 GAGGACGGGGAGGAGGAGGAGGCGGCGCCCGCGGACGCAGGGGCGTTCAATGCTCCAGTA 480
    GluAspGlyGluGluGluGluAlaAlaProAlaAspAlaGlyAlaPheAsnAlaProVal

481 ATAAACCGATTCACAAGGCGTGCCCTCAGTATGTGCAGAAGCTTATAATCCTGATGAAGAA 540
    IleAsnArgPheThrArgArgAlaSerValCysAlaGluAlaTyrAsnProAspGluGlu

541 GAAGATGATGCAGAGTCCAGGATTATACATCCAAAAACTGATGATCAAAGAAATAGGTTG 600
    GluAspAspAlaGluSerArgIleIleHisProLysThrAspAspGlnArgAsnArgLeu

601 CAAGAGGCTTGCAAAGACATCCTGCTGTTTAAGAATCTGGATCCGGAGCAGATGTCTCAA 660
    GlnGluAlaCysLysAspIleLeuLeuPheLysAsnLeuAspProGluGlnMetSerGln

661 GTATTAGATGCCATGTTTGAAAAATTGGTCAAAGATGGGGAGCATGTAATTGATCAAGGT 720
    ValLeuAspAlaMetPheGluLysLeuValLysAspGlyGluHisValIleAspGlnGly

721 GACGATGGTGACAACTTTTATGTAATTGATAGAGGCACATTTGATATTTATGTGAAATGT 780
    AspAspGlyAspAsnPheTyrValIleAspArgGlyThrPheAspIleTyrValLysCys

781 GATGGTGTTGGAAGATGTGTTGGTAACTATGATAATCGTGGGAGTTTCGGCGAACTGGCC 840
    AspGlyValGlyArgCysValGlyAsnTyrAspAsnArgGlySerPheGlyGluLeuAla

841 TTAATGTACAATACACCCAGAGCAGCTACAATCACTGCTACCTCTCCTGGTGCTCTGTGG 900
    LeuMetTyrAsnThrProArgAlaAlaThrIleThrAlaThrSerProGlyAlaLeuTrp
```

FIG. 3A

```
 901 GGTTTGGACAGGGTAACCTTCAGGAGAATAATTGTGAAAAACAATGCCAAAAAGAGAAAA  960
     GlyLeuAspArgValThrPheArgArgIleIleValLysAsnAsnAlaLysLysArgLys

961 ATGTATGAAAGCTTTATTGAGTCACTGCCATTCCTTAAATCTTTGGAGTTTTCTGAACGC 1020
     MetTyrGluSerPheIleGluSerLeuProPheLeuLysSerLeuGluPheSerGluArg

1021 CTGAAAGTAGTAGATGTGATAGGCACCAAAGTATACAACGATGGAGAACAAATCATTGCT 1080
     LeuLysValValAspValIleGlyThrLysValTyrAsnAspGlyGluGlnIleIleAla

1081 CAGGGAGATTCGGCTGATTCTTTTTTCATTGTAGAATCTGGAGAAGTGAAAATTACTATG 1140
     GlnGlyAspSerAlaAspSerPhePheIleValGluSerGlyGluValLysIleThrMet

1141 AAAAGAAAGGGTAAATCAGAAGTGGAAGAGAATGGTGCAGTAGAAATGCCTCGATGCTCG 1200
     LysArgLysGlyLysSerGluValGluGluAsnGlyAlaValGluMetProArgCysSer

1201 CGGGGACAGTACTTTGGAGAGCTTGCCCTGGTAACTAACAAACCTCGAGCAGCTTCTGCC 1260
     ArgGlyGlnTyrPheGlyGluLeuAlaLeuValThrAsnLysProArgAlaAlaSerAla

1261 CACGCCATTGGGACTGTCAAATGTTTAGCAATGGATGTGCAAGCATTTGAAAGGCTTCTG 1320
     HisAlaIleGlyThrValLysCysLeuAlaMetAspValGlnAlaPheGluArgLeuLeu

1321 GGACCTTGCATGGAAATTATGAAAAGGAACATCGCTACCTATGAAGAACAGTTAGTTGCC 1380
     GlyProCysMetGluIleMetLysArgAsnIleAlaThrTyrGluGluGlnLeuValAla

1381 CTGTTTGGAACGAACATGGATATTGTTGAACCCACTGCATGAAGCAAAAGTATGGAGCAA 1440
     LeuPheGlyThrAsnMetAspIleValGluProThrAlaEnd

1441 GACCTGTAGTGACAAAATTACACAGTAGTGGTTAGTCCACTGAGAATGTGTTTGTGTAGA 1500

1501 TGCCAAGCATTTTCTGTGATTTCAGGTTTTTTCCTTTTTTTACATTTACAACGTATCAAT 1560

1561 AAACAGTAGTGATTTAATAGTCAATAGGCTTTAACATCACTTTCTAAAGAGTAGTTCATA 1620

1621 AAAAAATCAACATACTGATAAAATGACTTTGTACTCCACAAAATTATGACTGAAAGGTTT 1680

1681 ATTAAAATGATTGTAATATATAGAAAGTATCTGTGTTTAAGAAGATAATTAAAGGATGTT 1740

1741 ATCATAGGCTATATGTGTTTTACTTATTCAGACTGATAATCATATTAGTGACTATCCCCA 1800

1801 TGTAAGAGGGCACTTGGCAATTAAACATGCTACACAGCATGGCATCACTTTTTTTTATAA 1860

1861 CTCATTAAACACAGTAAAATTTTAATCATTTTTGTTTTAAAGTTTTCTAGCTTGATAAGT 1920
```

FIG. 3B

```
1921 TATGTGCTGCCTTGGCCTATTGGTGAAATGGTATAAAATATCATATGCAGTTTTAAAACT 1980
1981 TTTTATATTTTTGCAATAAAGTACATTTTGACTTTGTTGGCATAATGTCAGTAACATACA 2040
2041 TATTCCAGTGGTTTTATGGACAGGCAATTTAGTCATTATGATAATAAGGAAAACAGTGTT 2100
2101 TTAGATGAGAGATCATTAATGCATTTTTCCCTCATCAAGCATATATCTGCTTTTTTTTAT 2160
2161 TTTGCAATTCTCTGTATTCTATGTCTTTAAAAATTTGATCTTGACATTTAATGTCACAAA 2220
2221 GTTTTGTTTTTTAAAAAGTGATTTAAACTTAAGATCCGACATTTTTGTATTCTTTAAG 2280
2281 ATTTTACACCTAAAAAATCTCTCCTATCCCAAAAATAATGTGGGATCCTTATCAGCATGC 2340
2341 CCACAGTTTATTTCTTTGTTCTTCACTAGGCCTGCATAATACAGTCCTATGTAGACATCT 2400
2401 GTTCCCTTGGGTTTCCGTTCTTTCTTAGGATGGTTGCCAACCCACAATCTCATTGATCAG 2460
2461 CAGCCAATATGGGTTTGTTTGGTTTTTTTAATTCTTAAAAACATCCTCTAGAGGAATAGA 2520
2521 AACAAATTTTTATGAGCATAACCCTATATAAAGACAAAATGAATTTCTGACCTTACCATA 2580
2581 TATACCATTAGGCCTTGCCATTGCTTTAATGTAGACTCATAGTTGAAATTAGTGCAGAAA 2640
2641 GAACTCAGATGTACTAGATTTTCATTGTTCATTGATATGCTCAGTATGCTGCCACATAAG 2700
2701 ATGAATTTAATTATATTCAACCAAAGCAATATACTCTTACATGATTTCTAGGCCCCATGA 2760
2761 CCCAGTGTCTAGAGACATTAATTCTAACCAGTTGTTTGCTTTTAAATGAGTGATTTCATT 2820
2821 TTGGGAAACAGGTTTCAAATGAATATATATACATGGGTAAAATTACTCTGTGCTAGTGTA 2880
2881 GTCTTACTAGAGAATGTTTATGGTCCCACTTGTATATGAAAATGTGGTTAGAATGTTAAT 2940
2941 TGGATAATGTATATATAAGAAGTTAAAGTATGTAAAGTATAACTTCAGCCACATTTTTAG 3000
3001 AACACTGTTTAACATTTTTGCAAAACCTTCTTGTAGGAAAAGAGAGCTCTCTACATGAAG 3060
3061 ATGACTTGTTTTATATTTCAGATTTTATTTTAAAAGCCATGTCTGTTAAACAAGAAAAAA 3120
3121 CACAAAAGAACTCCAGATTCCTGGTTCATCATTCTGTATTCTTACTCACTTTTTCAAGTT 3180
3181 ATCTATTTTGTTGCATAAACTAATTGTTAACTATTCATGGAACAGCAAACGCCTGTTTAA 3240
3241 TAAAGAACTTTGACCAAGAAAAAAAAAAAAAAAAAAAAAAAAAAAAAAAAAAAAAAAAAA 3300
3301 AAAAAAAAAAAAAAAAAAAAAAAAAAAAAAAAAAAAAAAAAAAA 3347
```

FIG. 3C

DNA FOR HUMAN REGULATORY SUBUNITS (RIα AND RIIβ) OF CAMP-DEPENDENT PROTEIN KINASES

CROSS REFERENCE TO RELATED APPLICATION(S)

This United States application stems from PCT International Application No. PCT/NO87/00069 filed Oct. 27, 1987.

BACKGROUND OF THE INVENTION

Cyclic AMP-dependent protein kinases play an important role in normal cell differentiation and cell replication. Many hormones/chemical substances affect cell metabolism and gene expression by regulating the level of intracellular cyclic AMP (cAMP), which in turn regulates the activity of cAMP-dependent protein kinases. The tetrameric holoenzyme of cAMP-dependent protein kinase consists of two identical regulatory (R) and catalytic (C) subunits. The catalytic subunits dissociate from the holoenzyme on the binding of two molecules of cAMP to each of the regulatory subunits. The free activated catalytic subunit phosphorylates serine and threonine residues on proteins and thereby mediates the biological response to the hormonal stimulus. It has further been shown that the free regulatory subunit may have a direct effect on the regulation of cellular functions independent of phosphorylation (Lohmann et al., 1984).

Originally two major types of cAMP-dependent protein kinases (types I and II) were described (Corbin et al., 1975). This classification was based on the sequential elution profile from DEAE-cellulose columns using increasing salt concentrations. These kinases were shown to be distinguished primarily by their regulatory subunits (RI and RII), which differ in their molecular weights, affinities for cAMP and cAMP analogues (Corbin et al., 1982; Robinson-Steiner and Corbin 1983), antigenicity (Fleischer et al., 1976; Kapoor et al., 1979; Lohmann et al., 1983) their ability to be autophosphorylated (Corbin et al., 1975; Hofmann et al., 1975; Rosen et al., 1975) and their amino acid sequences (Takio et al., 1984; Titani et al., 1984).

Recent studies, primarily involving cDNA cloning and sequencing, show a multiplicity in R and C subunit forms. Four different regulatory subunits (RIα, RIβ, RII$_{51}$ (RIIβ), and RII$_{54}$ (RIIα)) and two different catalytic subunits (Cα and Cβ) for cAMP-dependent protein kinases have now been identified at the gene/mRNA level. None of these have yet been characterized in human material at the gene/mRNA level. The bovine skeletal muscle type of RI (Titani et al., 1984), with an apparent molecular mass of 49 kD and found in most tissues, should now be designated RIα. Complementary DNA clones for this protein have been characterized (Lee et al., 1983). A second isoform of RI, (designated RIβ), which is only expressed in brain and germinal cells, has recently been identified by cDNA cloning from a mouse cDNA library (Dr. G. S. McKnight, unpublished data). For some time, two forms of RII have been recognized. A 54 kD form (rat) present in most tissues (Jahnsen et al., 1985; 1986a), has been designated RII$_{54}$ (RIIα), while a 51 kD form found in brain, granulosa cells, testis and adrenal tissue (Jahnsen et al., 1986a; 1986b) has been called RII$_{51}$ (RIIβ). A partial cDNA clone for RII$_{51}$ from rat granulosa cells has been described (Jahnsen et al., 1986b), and recently the cloning of RII$_{54}$ from rat skeletal muscle and mouse brain has been reported (Scott et al., 1987). To further complicate the picture, two different gene products for the C subunit have been revealed in mouse and bovine tissues (Uhler et al., 1986a; 1986b; Showers et al., 1986). These have been designated Cα and Cβ. In most tissues examined Cα mRNA is more abundant than Cβ mRNA.

A well defined domain structure appears to be retained in each R-subunit. The protein can be divided into thirds based on the amino acid sequence. The NH$_2$-terminal third of the molecule contains an essential recognition site for the C-subunit, and is also the major site of interaction between the two protomers of the R$_2$ dimer. The COOH-terminal two-thirds of the molecule contain repeating segments which represent the two cAMP-binding sites.

Cyclic AMP-dependent protein kinases have previously been reported to play a central role in connection with human diseases such as cystic fibrosis (Frizzell et al., 1986: Welsh and Lietke, 1986), cancer (e.g. breast cancer (Cho-Chung, 1985)) and skin diseases (e.g. psoriasis (Brion et al., 1986)). In these cases the protein products of the cAMP-dependent protein kinase genes have been studied. The methods which have been used in these protein studies have mainly been DEAE cellulose chromatography, assays of protein kinase activity, photoaffinity labelling using ($^{32}$P) azido-cAMP and immunological methods. The sensitivity and specificity of these methods of measurement make it difficult/impossible to distinguish the various gene products for cAMP-dependent protein kinases. Modern methods using recombinant DNA technology have enabled the applicants to identify and separate different subunits of cAMP-dependent protein kinases. These studies have been performed using bovine, rat and mouse material.

SUMMARY OF THE INVENTION

Before the priority data of the present application nobody has identified, isolated and characterized human genes for regulatory subunits of cAMP-dependent protein kinases. According to the present invention human genes for regulatory subunits (RIα and RIIβ) of cAMP-dependent protein kinases have been discovered, isolated and characterized. These genes (or DNA fragments derived from them) can for example be used for:

Characterization of mRNA and DNA for the gene in question in normal and pathological material using standard methods in recombinant DNA technology, such as RNA blot analysis (Northern) and DNA blot analysis (Southern).

Production of high amounts of normal (unmanipulated) or mutated R subunits in a heterologous system like E. coli.

This will e.g. allow studies on structure/function relationship and provide enough protein for assessment of 3-dimensional structure by X-ray crystallography. Having the 3-dimensional structure one can determine how and where cAMP binds to the different R's. From computer based analysis and molecular graphics it is possible to deduct the structure of cAMP-analogues (agonists and antagonists) which are specific for the different R's or specific for one of the two cAMP-binding sites on each R. If the assumption that different R's possess different functional qualities is correct, it may be possible to either stimulate or inhibit specific R's using cAMP agonists and antagonists, respectively. Such analogues can be used to manipulate cell differentiation and cell replication, processes in which cAMP-dependent protein kinases are known to play important roles. Thus, such analogues (drugs) may find their way into therapeutic use.

Production of specific antibodies to RIα and RIIβ using peptides produced or deduced from the nucleotide sequences of RIα and RIIβ.

EXPERIMENTAL PROCEDURES

Complementary DNA-cloning: A human testis cDNA library in lambda gt11 was obtained from Clontech, Palo Alto, Calif. (Cat#HL 1010). Phage plaques were transferred to nitrocellulose filters, denatured, baked, and prehybridized at 68° C. for 2 to 20 hours in 6×SSC, 2×Denhardt's solution (Maniatis et al., 1982). Hybridization was carried out in the same buffer at 68° C. with a nick-translated DNA probe. The filters were washed twice in 1×SSC, 0.5% SDS for two hours at 68° C. After washing the filters were dried and autoradiographed.

Nucleotide sequencing: Nucleotide sequencing was performed with the dideoxy chain termination method using standard conditions (Sanger et al., 1977).

Northern blot analysis: Total RNA from human testis and T-lymphocytes was isolated by the guanidinium isothiocyanate method of Chirgwin et al. (1979). Samples of total RNA were denatured in 50% (v/v) formamide, 6.0% formaldehyde, 2.4 mM Herpes, 0.6 mM sodium acetate and 0.12 mM EDTA at 50° C. for 15 minutes. Twenty μg of total RNA was resolved on a 1.5% agarose gel containing 6.7% formaldehyde (v/v) and 20 mM sodium phosphate buffer, pH 7.0. The gel was blotted onto a nylon membrane, and baked at 80° C. for 1 hour. After prehybridization in 5×Denhardt's solution, 5×SSC, 50 mM sodium phosphate buffer, pH 6.5, 0.1% SDS, 250 μg/ml salmon sperm DNA, and 50% (v/v) formamide, the filter was hybridized at 42° C. in the same buffer containing nick-translated probe (specific activity $4\times10^8$ dpm/μg DNA, $10^6$ cpm/ml hybridization solution). The membrane was washed four times in 2×SSC, 0.1% (w/v) SDS at room temperature for 5–10 minutes, followed by two washes using 0.1×SSC, 0.1% (w/v) SDS at 50° C. The membrane was autoradiographed using Kodak (XAR-5) or Hyperfilm MP (Amersham film).

RESULTS

Molecular Cloning, cDNA Structure and Deduced Amino Acid Sequence of RIα

Using a 0.6 kb Pst I-fragment from a mouse RIα cDNA as a probe 1 million recombinant clones from a human testis cDNA library were screened. Sixty-five positive clones were obtained. Complementary DNA clones were selected on basis of their lengths and sequenced. One clone contained the entire coding region for the human RIα subunit. The complete nucleotide sequence and the deduced amino acid sequence is shown in FIG. 1. The cDNA consists of a total 1476 nucleotides of which 102 are located 5' to the start codon. Including the start methionine, the coding region predicts a protein of 381 amino acids. The derived human RIα protein contains the same number of amino acids as the rat brain RIα (Kuno et al., 1987), but is one amino acid longer than the RIα from bovine skeletal RIα (Titani et al., 1984). Ser-5, which is present in both the human and the rat proteins, but is missing from the bovine RIα is responsible for the size difference.

At the nucleotide level the similarity in the coding region between human RIα and rat RIα is 88%. The differences are predominantly in the part of the cDNA corresponding to the N-terminal part of RIα and more than 80% of the differences are conservative third codon changes.

Northern blot analysis of RNA employing the full length human RIα cDNA as a probe revealed two major mRNA forms (1.5, 3.0 kb in size) in human testis (FIG. 2). In human T-lymphocytes, only the 3.0 kb mRNA was seen (FIG. 2). It is not finally determined whether the 3.0 kb mRNA codes for the same protein as the 1.5 kb mRNA. Two different polyadenylation site signals in the processing of mRNA, a phenomenon that has been reported for the rat granulosa cell RIIβ (Jahnsen et al., 1986b). The possibility that the two different mRNA species are transcribed from different genes, can still not be entirely excluded.

Molecular Cloning, cDNA Structure and Deduced Amino Acid Sequence of RIIβ

Approximately 1 million clones were screened from a human testis lambda gt11 expression cDNA library, using a $^{32}$P-labelled 1.5 kb rat RIIβ cDNA (Jahnsen et al., 1986b) as a probe. After screening and plaque purification, a total of three independent positive clones had been isolated. The clone containing the largest insert (3.3 kb) was digested with various restriction enzymes or exonucleases and the resulting fragments were subcloned into the sequencing vector M13 and sequenced using the Sanger dideoxy chain termination method. The resulting sequence is shown in FIG. 3 and reveals a full-length cDNA sequence containing the entire 1254 bp coding region, a 165 bp 5'-non-coding region and a 3'-non-coding region of 1836 bp followed by a polyA-tail. The 5'-non-translated region contains 86% G/C. The A/T-rich 3'-non-translated region of 1836 bp contains a total of seven polyadenylation site signals (these are underlined in FIG. 3).

The predicted protein encoded by the corresponding mRNA contains 418 amino acids including the start methionine (FIG. 3).

Northern blot analysis of RNA employing the full length human RIIβ cDNA as a probe revealed two major mRNA forms (approximately 1.7 and 3.3 kb in size) in human testis (data not shown).

DESCRIPTION OF THE FIGURES

FIG. 1—Nucleotide and deduced amino acid sequences of human RIα. The amino acids are shown in three letter code. Two potential polyadenylation signals (ATTAAA and AATAAA) are underlined.

FIG. 3—Nucleotide and deduced amino acid sequences of human RIIβ. The amino acids are shown in three letter code. Potential polyadenylation signals (ATTAAA and AATAAA) are underlined.

REFERENCES

Figure 2:
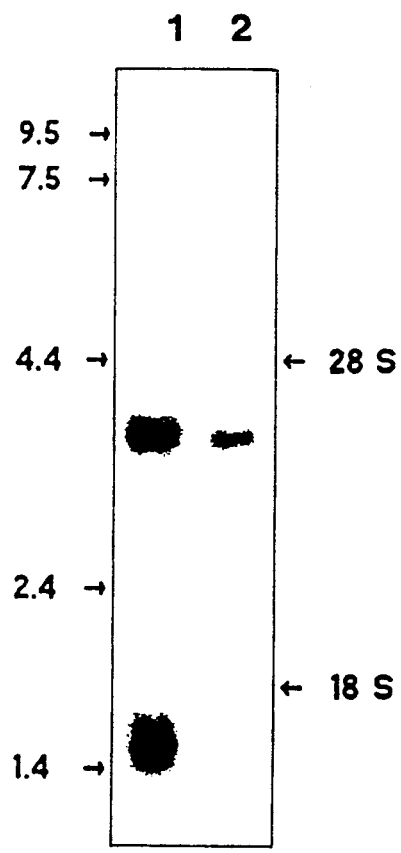
FIG. 2—Northern blot analysis of RNA from human testis and T lymphocytes. Twenty μg of total RNA form human testis (lane 1) and human T lymphocytes (lane 2) was electrophoresed, blotted on to a nylon membrane and hybridized with nick-translated human RIα probe as described in "EXPERIMENTAL PROCEDURES". The hybridizing bands were estimated to be 1.5 and 3.0 kb by comparison with RNA standards of 9.3, 7.5, 4.4, 2.4, and 1.4 kb from Bethesda Research Laboratories.

Brion D E, Raynaud R, Plet A, Laurent P, Leduc B, Anderson W (1986) Proc. Natl. Acad. Sci. USA 83: 5272

Chirgwin J M, Przybyla A E, MacDonald R J, Rutters W J (1979) Biochemistry 18: 5294

Cho-Chung Y S (1985) Genetic Engineering News 5:32

Corbin J D, Keely S L, Park S R (1975) J. Biol. Chem. 250: 218

Corbin J D, Rannels S R, Flockhart D A, Robinson-Steiner A M, Tigani M C, Doskeland S O, Suva R H, Suva R, Miller J P (1982) Eru. J. Biochem. 125: 259

Fleischer N, Rosen O M, Reichlin M (1976) Proc. Natl. Acad. Sci. USA 73: 54

Frizzell R A, Rechkemmer G, Shoemaker R L. (1975) Science 233: 558

Hofmann F, Beavo J A, Bechtel P J, Krebs E G (1975) J. Biol. Chem. 250: 7795

Jahnsen T, Lohmann S M, Walter U, Hedin L, Richards J S (1985) J. Biol. Chem. 260: 15980

Jahnsen T, Hedin L, Lohmann S M, Walter U, Richards J S (1986a) J. Biol. Chem. 261: 6637

Jahnsen T, Hedin L, Kidd V J, Beattie W G, Lohmann S M, Walter U, Durica J, Schulz T Z, Schiltz E, Browner M, Goldman D, Ratoosh S L, Richards J S (1986b) J. Biol. Chem. 261: 12352

Kapoor C L, Beavo J A, Steiner A L (1979) J. Biol. Chem. 254: 12427

Kuno T, Ono Y, Hirai M, Hashimoto S, Shuntoh H. Tanaka C. (1987) BBRC 146(2): 878

Lau Y-F, Kan Y W (1983) Proc. Natl. Acad. Sci. USA 80: 5225

Lee D C, Carmichael D F, Krebs E G, McKnight G S (983) Proc. Natl. Acad. Sci. USA 80: 3608

Lohmann S M, Schwoch G, Reiser G, Port R, Walter U (1983) EMBO J. 2: 153

Lohmann S M, Decamilli P, Einig I, Walter U (1984) Proc. Natl. Acad. Sci. USA 81: 6723

Maniatis T. Fritsch E F, Sambrook J (1982) Molecular Cloning. A Laboratory Manual. Cold Spring Harbor Laboratory.

Robinson-Steiner A M, Corbin J D (1983) J. Biol. Chem. 258:1032

Rosen O M, Ehrlichman J (1975) J. Biol. Chem. 250: 7788

Sanger F, Nicklen S, Coulson A R (1977) Proc. Natl. Acad. Sci. USA 74: 5463

Scott J D, Glaccum M B, Zoller M J, Uhler M D, Helfman D M, McKnight G S, Krebs E G (1987) Proc. Natl. Acad. Sci. USA 84: 5192

Showers M O, Maurer R A (1986) J. Biol. Chem. 261: 16288

Takio K, Smith S B, Krebs E G, Walsh K A, Titani K (1984) Biochemistry 23: 4200

Titani K, Sasagawa T, Ericsson L H, Kumar S, Smith S B, Krebs E G, Walsh K A (1984) Biochemistry 23: 4193

Uhler M D, Carmichael D F, Lee D C, Chrivia J C, Krebs E G, McKnight G S (1986a) Proc. Natl. Acad. Sci. USA 83: 1300

Uhler M D, Chrivia J C, McKnight G S (1986b) J. Biol. Chem. 261: 15360 welsh M J, Liedtke C M (1986) Nature 322: 467

I claim:

1. A biologically pure nucleic acid comprising DNA or RNA that encodes a regulatory subunit of a human cAMP-dependent protein kinases selected from the group consisting of RI$\alpha$ and RII$\beta$ as the molecule, wherein said DNA that encodes RI$\alpha$ has the nucleic acid sequence shown in FIG. 1 and the DNA that encodes RII$\beta$ has the nucleic acid sequence shown in FIG. 3.

2. The nucelic acid of claim 1, wherein said nucleic acid is cDNA.

3. The nucelic acid of claim 1, wherein said nucleic acid is mRNA.

* * * * *